United States Patent [19]

Wagnon et al.

[11] Patent Number: 4,840,935

[45] Date of Patent: Jun. 20, 1989

[54] PEPTIDE AMINO-ALCOHOL DERIVATIVES CONTAINING A TETRASUBSTITUTED CARBON ATOM, INHIBITING RENIN AND ACID PROTEASES, PROCESS FOR OBTENTION AND THERAPEUTICAL USE

[75] Inventors: Jean Wagnon, Montpellier; Remy Guegan, Castelnau-le-Lez; Colette LaCour, Montpellier; Dino Nisato, Saint-Georges d'Orques, all of France

[73] Assignees: Sanofi; Institut National de la Sante et de la Recherche Medicale, both of France

[21] Appl. No.: 886,070

[22] Filed: Jul. 16, 1986

[30] Foreign Application Priority Data

Jul. 31, 1985 [FR] France ................................. 8511728

[51] Int. Cl.$^4$ ........................ A61K 37/43; C07K 5/08
[52] U.S. Cl. ..................................... 514/18; 530/330; 530/331
[58] Field of Search .................. 514/18; 530/330, 331

[56] References Cited

FOREIGN PATENT DOCUMENTS 0192554 8/1986 European Pat. Off. .

OTHER PUBLICATIONS

J. Med. Chem. (1986) 29, 1152-9.
Chem. Abstr. vol. 101, (1984), 231034.
Chem. Abstr. vol. 99, (1983), 195412.
Chem. Abstr. vol. 105, (1986), 24620.
Chem. Abstr. vol. 105, (1986), 24630.
Chem. Abstr. vol. 105, (1986), 227324.
J. Med. Chem. (1986), 29, 1152-1159.

*Primary Examiner*—Delbert R. Phillips
*Attorney, Agent, or Firm*—Bacon & Thomas

[57] ABSTRACT

The present invention relates to peptide amino-alcohol derivatives containing a tetra substituted carbon atom. Said peptides inhibit the renin and acid proteases. The invention also relates to the process for their obtention and to pharmaceutical compositions.

13 Claims, No Drawings

PEPTIDE AMINO-ALCOHOL DERIVATIVES CONTAINING A TETRASUBSTITUTED CARBON ATOM, INHIBITING RENIN AND ACID PROTEASES, PROCESS FOR OBTENTION AND THERAPEUTICAL USE

The present invention relates to new peptide derivatives which inhibit renin and, more generally, acid proteases. It also relates to a process for their preparation and their application in therapy.

In 1970, UMEZAWA isolated a pentapeptide from a culture of streptomyces; this pentapeptide was called pepstatin and its structure was subsequently established and corresponds to the formula:

isovaleryl-L-valyl-L-valyl-statyl-L-alanyl-statin in which the name "statin" denotes the uncommon amino acid (3S,4S)-4-amino-3-hydroxy-6-methylheptanoic acid.

It has been shown that pepstatin inhibits acid proteases and is active especially against pepsin, cathepsin D and renin. In particular, renin, an enzyme originating from the kidney, is involved in the sequence angiotensinogen—angiotensin I—angiotensin II in the conversion of angiotensinogen to angiotensin.

As a powerful vasoconstrictor, angiotensin II plays a part in regulating the arterial pressure. The possibility of using pepstatin to combat arterial hypertension in man has been considered. However, since pepstatin acts on all acid proteases and has a low solubility in aqueous media and a low affinity for renin, its use in therapy has proved difficult. Pepstatin derivatives have been described in the scientific literature. For example, attempts have been made to solubilize pepstatin by lengthening the peptide chain (J. Cardiovasc. Pharmacol., 1980, 2, 687–698).

According to the present invention, it has been found possible to obtain very active products not by lengthening the peptide chain but by introducing hydrophilic residues onto various sites of a peptide analogous to pepstatin. This is all the more surprising because the prior art (U.S. Pat. No. 4470971 to Merck) teaches that the presence of hydrophilic substituents decreases the inhibitory activity towards renin.

The present invention relates to peptides having a high level of activity as inhibitors of renin and other acid proteases.

The following abbreviations will be used in the present description and in the claims:

Amino acids and protecting or activating groups

These abbreviations are consistent with those indicated by the Nomenclature Commission of IUPAC-IUB, Biochemistry Section. The most recent recommendations are reported in Eur. J. Biochem., 1984, 138, 5–7 and 9–37.

Amino Acids:

| | |
|---|---|
| Abu | alpha-aminobutyric acid |
| Ala | alanine |
| Asn | asparagine |
| Asp | aspartic acid |
| Cpg | cyclopentylglycine |
| Gln | glutamine |
| Gly | glycine |
| His | histidine |
| Ile | isoleucine |
| Leu | leucine |
| Met | methionine |
| Nle | norleucine |
| Nva | norvaline |
| Phe | phenylalanine |
| Phg | phenylglycine |
| Ser | serine |
| Val | valine |
| (tauMe)His | (tele-methyl)histidine |

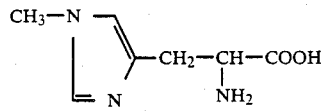

| | |
|---|---|
| (Pyr-3)Ala | (pyridin-3-yl)alanine |

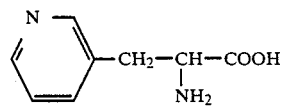

| | |
|---|---|
| (Benzimidazol-2-yl)Ala | |

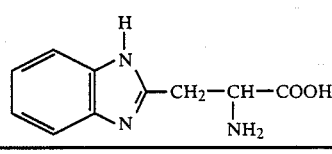

These amino acids are in the L configuration.

| | |
|---|---|
| Sta: | statin:4-amino-3-hydroxy-6-methylheptanoic acid |
| AHPPA: | 4-amino-3-hydroxy-5-phenylpentanoic acid |
| ACHPA: | 4-amino-5-cyclohexyl-3-hydroxypentanoic acid |

Unless indicated otherwise, Sta, AHPPA and ACHPA are in the 3S,4S configuration.

Protecting and activating groups:

| | |
|---|---|
| Ac: | acetyl |
| Boc: | tert.-butoxycarbonyl |
| (Boc)₂O: | bis(tert.-butocxycarbonic) anhydride |
| HONSu: | N—hydroxysuccinimide |
| OEt: | ethyl ester |
| OMe: | methyl ester |
| ONp: | p-nitrophenyl ester |
| ONSu: | N—hydroxysuccinimide ester |
| iVa: | isovaleryl |
| Z: | benzyloxycarbonyl |

The following abbreviations will also be used:

| | |
|---|---|
| AcOEt: | ethyl acetate |
| AcOH: | acetic acid |
| Bop: | benzyloxytrisdimethylaminophosphonium hexafluorophosphate |
| TLC: | thin layer chromatography |
| DCCI: | dicyclohexylcarbodiimide |
| DCHA: | dicyclohexylamine |
| DCU: | dicyclohexylurea |
| DIPEA: | diisopropylethylamine |
| DMF: | dimethylformamide |
| DMSO: | dimethyl sulfoxide |
| Ether: | ethyl ether |
| HOBt: | 1-hydroxybenzotriazole |
| MeOH: | methanol |
| NEM: | N—ethylmorpholine |
| NMM: | N—methylmorpholine |
| RT: | room temperature |
| TFA: | trifluoroacetic acid |

| | |
|---|---|
| -continued | |
| Reduced Sta: | 4-amino-6-methylheptane-1,3-diol |

The asymmetric carbons for which the configuration is determined are shown as C*.

The compounds according to the invention correspond to the following general formula:

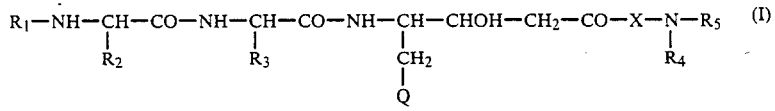

in which:

$R_1$ represents an acyl group chosen from the following groups: alkylcarbonyl, alkoxycarbonyl, arylcarbonyl, arylalkylcarbonyl, arylalkoxycarbonyl, heterocyclylcarbonyl, heterocyclylalkylcarbonyl, in which the alkyl group is optionally substituted by a hydroxyl group, heterocyclylcarbonylalkylcarbonyl, heterocyclylalkenylcarbonyl and cycloalkylcarbonyl, or represents a (lower alkyl)sulfonyl group which is unsubstituted or substituted on the alkyl by a free amino group or an amino group carrying a protecting group, or by a phenyl, or represents a phenylsulfonyl group which is unsubstituted or substituted on the phenyl nucleus by a lower alkyl;

$R_2$ represents a lower alkyl group which is unsubstituted or substituted by a phenyl, naphthyl, cyclohexyl or pyridyl, or $R_2$ represents a phenyl, naphthyl, cyclohexyl or pyridyl radical;

$R_3$ represents hydrogen a lower alkenyl, a phenyl, a naphthyl, a cycloalkyl containing 3 to 6 carbon atoms, a 5-membered or 6-membered monocyclic heterocyclic group which is unsubstituted or substituted with a lower alkyl or trifluoromethyl, or alternatively a lower alkyl which is unsubstituted or substituted by a free amino group or an amino group carrying a protecting group, by a di(lower alkyl)amino group, by a free carboxyl or a carboxyl esterified with a lower alkyl or a benzyl, by a free carbamoyl or a carbamoyl substituted with one or two lower alkyls or with a phenyl, by a hydroxyl, lower alkoxy or benzyloxy group, by a pyridylmethoxy group, by a (lower alkyl)thio, (lower alkyl)sulfinyl or (lower alkyl)sulfonyl group, by a phenyl which is unsubstituted or substituted with a hydroxyl, by a naphthyl, by a cycloalkyl containing from 3 to 6 carbon atoms, by a 5-membered or 6-membered monocyclic heterocyclic group which is unsubstituted or substituted with a lower alkyl or a trifluoromethyl, or by a bicyclic heterocyclic group which is unsubstituted or substituted with a lower alkyl or a trifluoromethyl;

Q represents isopropyl, phenyl or cyclohexyl, respectively forming with the radical:

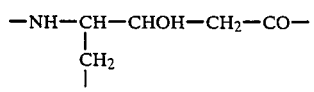

the residue of the amino acid Sta, AHPPA or ACHPA;

X is either a direct bond or the residue of an amino acid such as Ala, Nva, Val, Leu, Nle, Ile, Phg, Abu or Cpg;

$R_4$ represents hydrogen or a lower alkyl which is unsubstituted or substituted by an indolyl, pyridyl, imidazolyl or phenyl radical; and $R_5$ represents an aliphatic or cyclic hydrocarbon group of 3 to 20 carbon atoms which is unsubstituted or substituted by a phenyl, hydroxyphenyl or amino group, the said hydrocarbon group simultaneously containing at least one hydroxyl group and at least one carbon atom not having a C—H bond;

and also any pharmaceutically acceptable salts thereof with mineral or organic acids or alkali metals or alkaline earth metals.

The preferred products according to the present invention have the formula (I) above in which $R^5$ represents:

(a) a group:

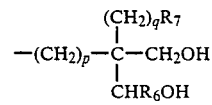

in which:

p represents an integer between zero and 5, q represents an integer between 0 and 5, $R_6$ represents hydrogen or a lower alkyl, and $R_7$ represents hydrogen, a hydroxyl group, an amine group, a carboxyl group, a pyridyl group or a phenyl group which is unsubstituted or substituted by a hydroxyl, with the proviso that if q=0, $R_7$ is different from hydrogen; or (b) a group:

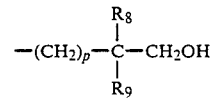

in which:

p is as defined above, $R_8$ represents a lower alkyl, and $R_9$ represents a lower alkyl which is unsubstituted or substituted by a free amino group or an amino group carrying a protecting group, or $R_8$ and $R_9$ together form a cycloalkyl of 3 to 8 carbon atoms with the carbon to which they are joined.

The compounds of the invention preferably contain from 1 to 3 hydroxyl groups in the radical $R_5$.

Particularly preferred products of the formula (I) above are those in which $R_5$ is a group chosen from:

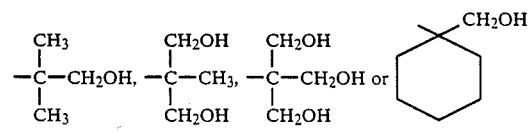

In the present description, the term "alkyl" denotes saturated or unsaturated alphatic hydrocarbon radicals containing from 1 to 10 carbon atoms, the preferred alkyl groups being the lower alkyls as defined below.

The expressions "lower alkyl" and "lower alkenyl", as used here, denote saturated or unsaturated aliphatic hydrocarbon radicals containing up to 6 carbon atoms.

The expressions "lower alkoxy" and "(lower alkyl)thio" represent hydroxyl and thiol groups substituted by a lower alkyl group as defined above.

The expression "5-membered or 6-membered monocyclic heterocycle" includes pyrrolidine, imidazole, thiazole, thiophene, furan, pyrrole, triazole, oxazole, isoxazole, pyridine and thiadiazoles.

The expression "bicyclic heterocycle" includes benzimidazole, benzothiazole, benzoxazole, indole or their hydrogenated homologs.

The expression "protecting group" is understood as meaning a protecting group normally used in peptide chemistry, for example Boc, Z or iVa.

The expression "acyl group" used to define $R_1$ includes the residues of aliphatic, alicyclic, aromatic or heterocyclic carboxylic acids. Preferred acyl groups are the residue of esterified carbonic acid, especially the groups Boc and Z, the residue of alkanoic acids containing from 2 to 6 carbon atoms, especially the group iVa, the residue of cyclohexylcarboxylic acid, the residue of phenylaliphatic acids, especially the phenylacetyl, 3-phenylpropionyl and dibenxylacetyl groups, the residue of arylcarboxylic acids, such as naphthoic acid, biphenylcarboxylic acid and benzoic acid which is unsubstituted or substituted on the phenyl nucleus, especially in the benzoyl group, the residue of a carboxylic acid in which the carboxyl is bonded to a 5-membered or 6-membered monocyclic heterocycle, especially the picolinoyl, nicotinoyl and isonicotinoyl groups, and the residue of alkanoic or alkenoic acids, such as acetic acid, propionic acid, butyric acid, valeric acid and their omega-hydroxy or omega-oxo derivatives substituted in the omega position by a 5-membered or 6-membered monocyclic heterocycle, as exemplified above.

More particularly, the present invention relates preferentially to the peptide amino alcohols of the formula I in which $R_2$, $R_3$, Q, $R_4$ and $R_5$ are as defined above and $R_1$ represents one of the following groups:

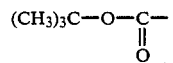

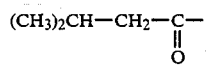

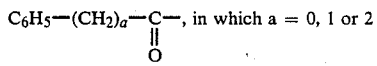

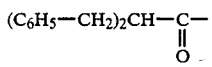

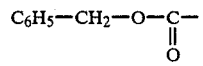

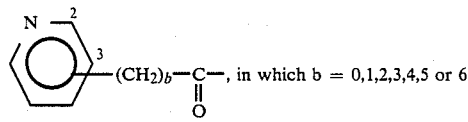

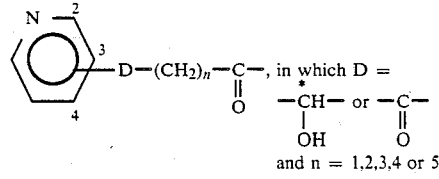

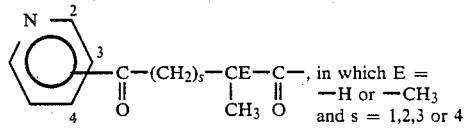

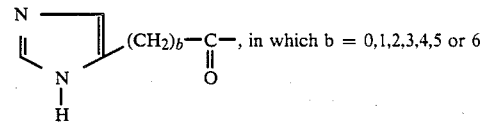

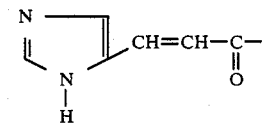

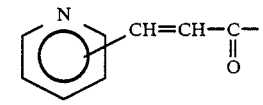

$NH_2CH_2CH_2—SO_2—$
$BocNHCH_2CH_2—SO_2—$
$ZNHCH_2CH_2—SO—$
$A—SO_2—$, in which A is a lower alkyl
$C_6H_5—(CH_2)_a—SO_2—$, in which a = 0, 1 or 2

Particular preference is given to the peptide amino alcohols of the formula (I) in which $R_2$, $R_3$, Q, $R_4$ and $R_5$ are as defined above and $R_1$ represents a group chosen from:
  isovaleryl,
  4-(pyridin-2-yl)-4-oxobutyryl,
  4-(pyridin-2-yl)-4-hydroxybutyryl,
  3-(pyridin-3-yl)propionyl,
  4-(pyridin-3-yl)butyryl,
  nicotinoyl and
  benzenesulfonyl.

Particular preference is also given to the compounds of the formula (I) in which $R_1$, $R_2$, $R_4$, $R_5$ and Q are as defined above and $R_3$ is such that the residue —NH—CH($R_3$)—CO— represents the residue (tauMe)His.

Another class of preferred compounds of the invention consists of the compounds of the formula (I) in which:

$R_1$ represents a group chosen from the following groups: isovaleryl, tert.-butoxycarbonyl, 3-(pyridin3-yl)propionyl, 4-(pyridin-3-yl)butyryl and nicotinoyl;

$R_2$ represents a benzyl;

$R_3$ represents n-butyl or a methyl substituted by a heterocyclic radical chosen from imidazol-4-yl, 1-methylimidazol-4-yl, 2-methylimidazol-4-yl, pyridin-3-yl and benzimidazol-2-yl;

$R_4$ is hydrogen;

X represents the residue of one of the amino acids Ile or Ala; and

Q and $R_5$ are as defined above.

The products according to the invention can be prepared by the methods normally used in peptide chemistry. Thus, according to another feature, the invention relates to a process for the preparation of the peptide amino-alcohol derivatives of the formula I above, wherein an amino alcohol of the formula:

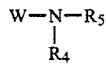

in which W is a protecting group or hydrogen and $R_4$ and $R_5$ are as defined above, and in which the hydroxyl groups are optionally protected, is treated with a lower alkyl ester of the amino acid of the formula: protected

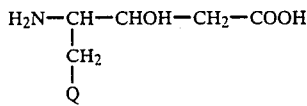

or H—X'—OH
in which X' has the definition given above for X, but X' is other than a direct bond, and Q is as defined above, the peptide chain is then lengthened in a stepwise fashion by coupling with the next, appropriately protected amino acids or fragments, the various operations being carried out using either an activated ester of the amino acid or fragment to be coupled or the N-protected amino acid in the presence of DCCI, and the N-protecting groups being cleaved after each coupling, either by hydrogenolysis or by hydrolysis in a strong acid medium, and, if appropriate, the hydroxyl groups of the resulting amino alcohol are deprotected by acid hydrolysis and, if necessary, the product thus obtained is converted to one of its pharmaceutically acceptable salts.

If the amino acid to be introduced into the sequence has a reactive group in its side chain, the said group should be blocked by an appropriate protecting group, which is subsequently removed.

The protection of the N-terminal amino acid by the group $R_1$ is carried out by known methods, either before the residue:

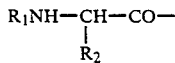

is coupled with the next amino acid, or after coupling.

If the compound (I) carries a substituent $R_3$ such that the corresponding residue is an unnatural amino acid, this unnatural amino acid is prepared by known methods. It is then coupled with the next amino acid by the usual method.

The amino alcohol part is prepared by coupling an appropriately chosen amino alcohol with the desired amino acid. If the chosen amino alcohol is not commercially available, it can be prepared by reduction of the corresponding amino acid ester.

Like pepstatin, the compounds of the present invention have a marked inhibitory action on acid proteases; in particular, they have a very strong inhibitory action on human plasma renin activity, which in general is considerably greater than that of the natural product: pepstatin.

The products according to the invention were studied for their therapeutic properties and especially their inhibitory action on enzymes. More particularly, the compounds were evaluated "in vitro" in terms of their inhibition of human plasma renin activity (PRA).

I-METHOD OF EVALUATION

The method of evaluation is based on that of GUYENE (J. Clin. Endocrinol. Metab., 1976, 43, 1301). The inhibition of PRA is evaluated from a human plasma pool rich in renin (15 to 20 mg of angiotensin I released per milliliter per hour), incubated for 60 minutes at 37° C., in a phosphate buffer at pH 7.4, in the presence of increasing concentrations of the product to be studied.

Human plasma contains the substrate angiotensinogen and the enzyme:renin. The angiotensin I released during the reaction is measured by radioimmunoassay: Plasma Renin Activity Kit from Travenol (nos. CA 533, 553). An inhibitor of the conversion enzyme, phenylmethylsulfonyl fluoride (PMSF), is added to the incubation medium. The total incubation volume is 555 microliters made up as follows:

420 microliters of human plasma 11 to 50 microliters of the product to be studied, at variable concentrations 119 to 80 microliters of phosphate buffer 5 microliters of PMSF.

A 1N solution of acetic acid in methanol (19/1 by volume) and a 1N solution of sodium hydroxide in methanol (2/1 by volume) are prepared. In a mixture of equal volumes of these 2 solutions, a 0.001M stock solution of the product to be studied is prepared. The subsequent dilutions are then made up in the phosphate buffer. The quantity of solvent present in a solution does not interfere with the results.

II-RESULTS

The results are expressed as the dose of compound, evaluated in mol, which causes a 50% inhibition ($IC_{50}$) of the human plasma renin activity (PRA) observed in the absence of inhibitor.

The results obtained with various products of the invention are given in the following Table 1, which shows the $IC_{50}$ values of each molecule in terms of their inhibition of human plasma renin activity at pH 7.4. From 5 to 10 doses were required in order to determine these $IC_{50}$ values. Pepstatin, used as the reference substance, is always tested in parallel in each experiment. The results are expressed as their logarithmic value (-log $IC_{50}$).

TABLE 1

| SR no. | Inhibition of human PRA -log $IC_{50}$ pH 7.4 |
|---|---|
| Pepstatin | 4.92 |
| 43 574 | 8.58 |
| 43 576 | 8.40 |
| 43 603 | 9.32 |
| 43 686 | 8.22 |
| 43 707 | 8.45 |
| 43 721 | 8.11 |
| 43 737 | 8.67 |
| 43 763 | 7.11 |
| 43 799 | 8.26 |
| 43 808 | (a) |

TABLE 1-continued

| SR no. | Inhibition of human PRA -log IC$_{50}$ pH 7.4 |
|---|---|
| 43 842 | (a) |
| 43 845 | (a) |
| 43 860 | 7.48 |
| 43 925 | (a) |
| 43 966 | 7.72 |
| 43 972 | (b) 7.88 |
| 44 094 | 7.74 |
| 44 125 | 7.44 |

(a) means that the inhibition of human PRA is about 90% when the concentration of the product is $10^{-10}$ molar.
(b) means that the inhibition of PRA was measured on baboon plasma.

The particularly high inhibitory activity of the products according to the invention can be seen from this table.

The toxicity of the products according to the invention is compatible with their use in therapy.

It is therefore possible to consider using the products according to the invention in areas of therapy where the inhibition of renin-angiotensin enzyme systems is justified, especially arterial hypertension, gastroduodenal ulcers and inflammatory complaints.

Thus, according to another feature, the present invention relates to antihypertensive drugs in which the peptides of the formula (I) or their pharmaceutically acceptable salts are present as active principles.

The peptide amino alcohols of the present invention can be administered in therapy by intravenous, intramuscular or subcutaneous injection. They are used in a solvent such as physiological serum (isotonic saline solution) or in a buffer such as phosphate buffer; they can also be suspended in a pharmaceutically acceptable aqueous or non-aqueous diluent. Each dosage unit can contain from 1 to 1000 mg of active principle.

The non-limiting examples which follow are given in order to illustrate the present invention.

The pH of the solutions in an organic solvent is measured or checked using moist pH indicator paper.

The indicated melting points (m.p.) are taken from triturated solids; they are measured by the capillary tube method.

The specific rotations ([α]$_D$) are measured at 25° C.

To run the infrared (IR) spectra, the product is dissolved in CH$_2$Cl$_2$ or mixed with KBr to form a disk.

Finally, the nuclear magnetic resonance (NMR) spectra are run at 250 MHz in DMSO solution with hexamethyldisiloxane as the internal standard.

The following abbreviations are used:

| | |
|---|---|
| s: | singlet |
| d: | doublet |
| m: | multiplet or unresolved signals. |

Also,
H ar denotes aromatic H
H im denotes H of the imidazole
H pyr denotes H of the pyridine
H (reduced Sta) denotes H of 4-amino-6-methylheptane-1,3-diol in the 3R,4S or 3S,4S configuration
approx. means approximately.
The chemical shifts (delta) are measured in ppm.

EXAMPLE 1:

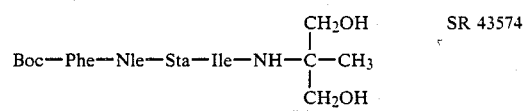

(1°) Boc-Nle-Sta-OCH$_3$

A solution of Boc-Nle-ONSu (900 mg), HOBt (421 mg) and TFA-Sta-OCH$_3$ (0.9 equivalent), containing sufficient NMM to bring the pH of the solution to about 7, is reacted in a mixture of equal volumes of CH$_2$Cl$_2$ and dioxane (16 ml). After 18 hours, the mixture is evaporated to dryness, water is added, extraction is carried out with ether and the organic phase is washed successively with a solution of KHSO$_4$, water, a solution of NaHCO$_3$ and then a saline solution. After drying (MgSO$_4$) and evaporation, an oil is isolated which is purified by chromatography on silica gel (eluent: pentane/ethyl acetate, 1/1 by volume). Yield 85%.

M.p. = 79°–81° C. after trituration in a CH$_2$Cl$_2$/ether mixture.

[α]$_D$ = −53.1 (c = 1; MeOH).

NMR SPECTRUM

| Delta | Appearance | Protons | Assignment |
|---|---|---|---|
| 7.16 | d, J = 9 Hz | 1 H | NHCO |
| 6.82 | d, J = 8 Hz | 1 H | NHCO$_2$ |
| 5.0 | d, J = 4 Hz | 1 H | OH |
| 3.88–3.67 | m | 3 H | CH (alpha) (Nle), C$\underline{H}$NH, C$\underline{H}$OH |
| 3.50 | s | 3 H | OCH$_3$ |
| 2.39–2.07 | m | 2 H | CH$_2$CO (Sta) |
| 1.65–1.07 | m | 18 H | (CH$_3$)$_3$C, CH, CH$_2$ |
| 0.84–0.71 | m | 9 H | CH$_3$ (Nle and Sta) |

(2°) Boc-Phe-Nle-Sta-OCH$_3$

The peptide Boc-Nle-Sta-OCH$_3$ (800 mg) is treated at 0° C. for 10 minutes in TFA (8 ml) and the excess solvent is then evaporated off at RT under vacuum in a Büchi Rotavapor. A solution of Boc-Phe-ONp (924 mg), HOBt (384 mg) and NMM (400 mg), prepared in CH$_2$Cl$_2$ (15 ml), is added at 0° C. to the salt thus obtained and the pH of the reaction medium is then brought to about 7 by the addition of a further quantity of NMM. After 24 hours, the mixture is evaporated to dryness, water is added, extraction is carried out with AcOEt and the organic phase is washed with a solution of KHSO$_4$, several times with a solution of Na$_2$CO$_3$ and with an aqueous saline solution and then dried (MgSO$_4$). After evaporation of the solvent and filtration on silica gel (eluent: pentane/ethyl acetate, 4/6 by volume), the expected compound is isolated in the form of a white powder. Yield 69%.

M.p. = 126°–129° C. after recrystallization from a CH$_2$Cl$_2$/hexane mixture.

[α]$_D$ = −37.2 (c = 1; MeOH).

NMR SPECTRUM

| Delta | Appearance | Protons | Assignment |
|---|---|---|---|
| 7.83 | d, J = 8 Hz | 1 H | NHCO |
| 7.49 | d, J = 8 Hz | 1 H | NHCO |
| 7.27–7.04 | m | 5 H | C$_6$H$_5$ |
| 6.93 | d, J = 8 Hz | 1 H | NHCO$_2$ |
| 4.98 | d, J = 4 Hz | 1 H | OH |

| NMR SPECTRUM | | | |
|---|---|---|---|
| Delta | Appearance | Protons | Assignment |
| 4.29–4.14 | m | 1 H | CH (alpha) |
| 4.14–4 | m | 1 H | CH (alpha) |
| 3.88–3.70 | m | 2 H | CH—NH— and CHOH (Sta) |
| 3.50 | s | 3 H | OCH$_3$ |
| 2.95–2.56 | m | 2 H | CH$_2$C$_6$H$_5$ |
| 2.37–2.08 | m | 2 H | CH$_2$CO (Sta) |
| 1.67–1.10 | m | 18 H | (CH$_3$)$_3$C, CH$_2$ (Nle), CH, CH$_2$ (Sta) |
| 0.86–0.70 | | 9H | CH$_3$ |

(3°) Boc-Phe-Nle-Sta-OH

The previous solid (750 mg) is hydrolyzed at RT with sodium hydroxide (1.3 equivalents) in a mixture of water (5 ml) and dioxane (10 ml) for 3 hours. The mixture is evaporated to dryness in a Büchi Rotavapor at RT, water is then added, the mixture is acidified with a solution of KHSO$_4$ and extracted with 3 volumes of AcOEt, and the extract is washed with an aqueous saline solution and dried (MgSO$_4$). After evaporation of the solvent, a solid is isolated (yield 95%) which is used as such for the subsequent reactions. NMR shows that the peak at 3.50 ppm has totally disappeared.

[α]$_D$ = −37.0 (c=1; MeOH).

(4°) 2-(Boc-isoleucylamino)-2-methylpropane-1,3-diol

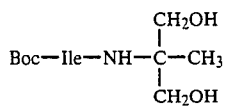

320 mg of 2-amino-2-methylpropane-1,3-diol are dissolved in 20 cm$^3$ of a mixture of equal volumes of DMF and CH$_2$Cl$_2$; 1 g of Boc-Ile-ONSu is added and the reaction is left to proceed for 18 hours at RT, with stirring; a further 320 mg of 2-amino-2-methylpropane-1,3-diol are added and the reaction is then left to proceed for 72 hours at RT, with stirring. The mixture is evaporated to dryness and the crude reaction product is chromatographed on silica, eluting with a chloroform/AcOEt mixture, 1/9 by volume, to give 617 mg of the expected product.

M.p. = 123°–126° C.

(5°) SR 43574

125 mg of the compound obtained above are treated at 0° C. in TFA for 15 minutes. After evaporation of the excess solvent and washing of the salt with ether, a solution of this salt in the minimum quantity of acetonitrile is added to a solution of 200 mg of the peptide Boc-Phe-Nle-Sta-OH in 10 ml of acetonitrile, the pH being kept at about 7–8 by the addition of the necessary quantity of NMM. 173 mg of Bop are then added and the reaction is left to proceed for 24 hours. After evaporation of the solvent, the crude reaction product is taken up with water and extracted with AcOEt. The extract is washed with a solution of NaHCO$_3$, a solution of KHSO$_4$ and a saline solution and dried, and the solvent is then evaporated off; after drying and evaporation of the solvent, the product is crystallized from an AcOEt/hexane mixture and then chromatographed on silica and recrystallized from a CH$_2$Cl$_2$/isopropyl ether mixture.

Weight = 171 mg.

m.p. = 107°–110° C.

| NMR SPECTRUM | | | |
|---|---|---|---|
| Delta | Appearance | Protons | Assignment |
| 8.0–7.48 | 3 d, J approx. 8 Hz | 3 H | NHCO |
| 7.06–7.30 | m | 6 H | C$_6$H$_5$, NHCO (diol) |
| 6.96 | d, J approx. 8 Hz | 1 H | NHCO$_2$ |
| 4.86 | d, J approx. 4 Hz | 1 H | OH (Sta) |
| 4.71 | t, J approx. 4 Hz | 2 H | OH (diol) |
| 4.29–3.66 | m | 5 H | CH (alpha), CH (OH) |
| 3.50–3.25 | m | 4 H | (CH$_2$)$_2$—OH |
| 2.97–2.57 | m | 2 H | CH$_2$C$_6$H$_5$ |
| 2.20–2.00 | m | 2 H | CH$_2$CO |
| 1.70–1.00 | m | 21 H | C(CH$_3$)$_3$, CH$_2$ (Nle), CH, CH$_2$ (Sta and Ile) |
| 1.08 | s | 3 H | CH$_3$ |
| 0.91–0.68 | m | 15 H | CH$_3$ (Nle, Sta, Ile) |

EXAMPLE 2

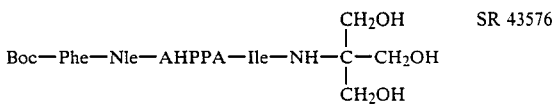

(1°) Boc-Nle-AHPPA-OCH$_3$

Boc-AHPPA-OCH$_3$ (3.0 g) is dissolved in TFA (20 ml) by the usual technique and the salt obtained is dissolved in CH$_2$Cl$_2$ and then neutralized at 0° C. with NMM. Boc-Nle-ONSu (3.3 g) and HOBt (1.6 g) are subsequently added to the reaction medium, which is then stirred for 18 hours at RT, the pH of the solution being kept at about 7–8 by the addition of further quantities of NMM. After the usual treatments, the residue is chromatographed on silica gel (eluent: CH$_2$Cl$_2$/AcOEt, 1/1 by volume). The peptide crystallizes on evaporation of the solvent in a Büchi Rotavapor in the cold (yield 80%).

M.p. = 89°–90° C.

IR (CH$_2$Cl$_2$): 3420-1715-1675 cm$^{-1}$

[α]$_D$ = −61.5 (c=1; MeOH).

(2°) Boc-Phe-Nle-AHPPA-Och$_3$

The previous compound (3.5 g) is dissolved at 0° C. in TFA (30 ml). The salt obtained by evaporation of the excess reactant by the usual method is dissolved in CH$_2$Cl$_2$, neutralized at 0° C. with NMM and then added at 0° C. to a previously prepared solution of Boc-Phe-ONp (3.3 g), HOBt (1.33 g) and NMM (808 mg) in CH$_2$Cl$_2$. The mixture is stirred for 18 hours at RT and the organic phase is then washed with water, a solution of Na$_2$CO$_3$, a solution of KHSO$_4$ and water and subsequently dried (MgSO$_4$). On evaporation of the solvent, a solid is isolated which is triturated in ether and then filtered off; it is homogeneous in TLC. Yield 75%.

M.p. = 182°–183° C.

[α]$_D$ = −50.7 (c=1; MeOH).

| NMR SPECTRUM | | | |
|---|---|---|---|
| Delta | Appearance | Protons | Assignment |
| 7.27–7.04 | m | 10 H | ar |
| 5.23 | d, J = 4 Hz | 1 H | OH |

| NMR SPECTRUM | | | |
|---|---|---|---|
| Delta | Appearance | Protons | Assignment |
| 4.27–3.80 | m | 4 H | CH (alpha) (Phe and Nle), CHNH and CHOH |
| 3.49 | s | 3 H | OCH$_3$ |
| 1.61–1.00 | m | 15 H | |
| 0.80 | t, J = 6 Hz | 3 H | CH$_3$ (Nle) |

(3°) Boc-Phe-Nle-AHPPA-OH

A solution of the ester described in the previous step (2 g) in dioxane (100 ml) is hydrolyzed at RT for 4 hours with a solution of sodium hydroxide (178 mg) in water (10 ml). Subsequent treatment according to Example 1, step 2, gives the acid, which is triturated in isopropyl ether, filtered off and dried in vacuo (yield 95%).
M.p.=161°–162° C.

(4°) 2-(Boc-isoleucylamino)-2-hydroxymethylpropane-1,3-diol

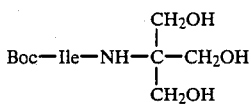

A suspension of tris(hydroxymethyl)aminomethane (1.32 g) in 40 ml of DMF is added to a solution of Boc-Ile-ONSu in DMF (10 ml). After stirring for 18 hours, the mixture is concentrated in vacuo, the concentrate is taken up with water, extraction is carried out with AcOEt and the extract is dried and concentrated. The concentrate is chromatographed on silica, eluting with an AcOEt/MeOH mixture, 9/1 by volume. The expected product is collected; it crystallizes from a CH$_2$Cl$_2$/ isopropyl ether mixture.
Weight=247 mg.
m.p.=122°–124° C.
[α]$_D$=−24.0 (c=0.41; MeOH).

(5°) SR 43576

The Boc group is removed in the usual way, with TFA, from 218 mg of the compound obtained above. The solid obtained is taken up with CH$_2$Cl$_2$, 4 ml of DMF are added, the solution is neutralized in the cold by the addition of a sufficient quantity of DIPEA, the peptide Boc-Phe-Nle-AHPPA-OH (369 mg) and Bop (287 mg) are then added and the mixture is stirred for 18 hours at RT, the pH being kept about 7. The mixture is concentrated in vacuo (pressure: 5 mm Hg), the concentrate is taken up with CH$_2$Cl$_2$ and the mixture is washed with water, a solution of Na$_2$CO$_3$ and a solution of KHSO$_4$ and then dried and concentrated. The solid obtained is chromatographed on silica, eluting with a chloroform/ methanol mixture, 95/5 by volume. The expected product is recrystallized from a hexane/ether mixture.
Weight=265 mg.
m.p.=94°–95° C.

| NMR SPECTRUM | | | |
|---|---|---|---|
| Delta | Appearance | Protons | Assignment |
| 7.96–7.65 | m | 3 H | NHCO |
| 7.29–7.00 | m | 11 H | C$_6$H$_5$ + NHCO |
| 6.95 | d, J = 8 Hz | 1 H | NHCO$_2$ |
| 5.07 | d, J approx. 4 Hz | 1 H | OH$^2$ |
| 4.63 | t, J approx. 4 Hz | 3 H | CH$_2$—OH |
| 4.30–3.75 | m | 5 H | CH (alpha), CHOH |
| 3.57–3.38 | m | 6 H | (CH$_2$)$_3$OH |
| 2.95–2.50 | m | 4 H | CH$_2$C$_6$H$_5$ |
| 2.30–2.00 | m | 2 H | CH$_2$CO |
| 1.68–0.93 | m | 18 H | C(CH$_3$)$_3$, CH$_2$ (Nle), CH, CH$_2$ (Ile) |
| 0.86–0.66 | m | 9 H | CH$_3$ (Ile, Nle) |

EXAMPLE 3

3-(Pyridin-3-yl)propionyl-Phe—Nle—AHPPA—Ile—NH— 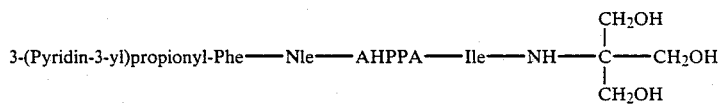

SR 43603

The Boc group is removed in the usual way, with TFA, from 240 mg of the SR 43576 prepared in the previous example. After evaporation of the excess solvent in vacuo, a residue is obtained which is taken up with CH$_2$Cl$_2$, 5 ml of DMF are added, the mixture is neutralized in the cold by the addition of a sufficient quantity of DIPEA, and 68 mg of 3-(pyridin-3-yl)propionic acid and 84 mg of Bop are then added. The mixture is stirred for 18 hours at RT, the pH being kept at about 7 by the addition of DIPEA. It is concentrated in vacuo (pressure=5 mm Hg), the concentrate is taken up with AcOEt and the mixture is washed with an aqueous carbonate solution and water and then dried and concentrated. After chromatography on silica, eluting with a CHCl$_3$/MeOH mixture, 9/1 by volume, the expected product is collected; it solidifies from a hexane/ ether mixture.
Weight=135 mg.
m.p.=90°–92° C.

| NMR SPECTRUM | | | |
|---|---|---|---|
| Delta | Appearance | Protons | Assignment |
| 8.34–7.00 | m | 19 H | C$_5$H$_4$N, C$_6$H$_5$, NHCO |
| 5.09 | d, J approx. 4 Hz | 1 H | OH (AHPPA) |
| 4.64 | t, J approx. 4 Hz | 3 H | OH (triol) |
| 4.57–3.70 | m | 5 H | CH (alpha) (Phe, Nle, Ile), CHOH and CHNH (AHPPA) |
| 3.57–3.38 | m | 6 H | CH$_2$OH |
| 2.96–2.50 | m | 6 H | CH$_2$—C$_5$H$_4$N, CH$_2$—C$_6$H$_5$ (Phe), CH$_2$—C$_6$H$_5$ (AHPPA) |
| 2.34–2.00 | m | 4 H | CH$_2$CO (AHPPA), C$_5$H$_4$NCH$_2$—CH$_2$CO |
| 1.68–0.92 | m | 9 H | CH$_2$ (Nle), CH and CH$_2$ (Ile) |
| 0.86–0.66 | m | 9 H | CH$_3$ (Nle, Ile) |

EXAMPLE 4

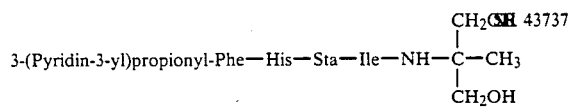

(1°) 3-(Pyridin-3yl)propionyl-Phe-His-Sta-OCH₃

500 mg of Boc-Phe-His-Sta-OCH₃ are treated at 0° C. for 5 minutes with 5 ml of TFA; the mixture is evaporated to dryness and the salt is then precipitated in ether. The salt is taken up with 15 ml of acetonitrile, 132 mg of 3-(pyridin-3-yl)propionic acid and 385 mg of Bop are then added and the mixture is neutralized to about pH 7 by the addition of DIPEA. After 24 hours, it is evaporated to dryness, an aqueous carbonate solution is added and extraction is carried out with AcOEt. The organic phase is washed several times with a solution of Na₂CO₃, water and then an aqueous saline solution, dried (MgSO₄) and then evaporated to dryness. The residue is dissolved in a 3M solution of KHSO₄ and the impurities are extracted with ether. The aqueous phase is neutralized with a solution of NaHCO₃. The precipitate is extracted with several volumes of AcOEt and the organic phase is washed with a solution of Na₂CO₃ and an aqueous saline solution and then dried (MgSO₄) and evaporated. A white solid is isolated which is recrystallized from a methanol/isopropyl ether mixture.

Weight=97 mg;
m.p.=168°-170° C;
[α]$_D$= −30.6 (c=1; MeOH).

(2°) 2-(Boc-isoleucylamino)-2-methylpropane-1,3-diol

This compound is obtained in Example 1, step 4.

(3°) SR 43 737

76.5 mg of the compound obtained in step 1 are dissolved in 6 ml of a methanol/water mixture (5/1 by volume), 5 drops of 30% sodium hydroxide solution are added and the mixture is left in a refrigerator overnight. It is acidified to about pH 3 by the addition of a solution of KHSO₄ and evaporated to dryness. A suspension of the dry residue in 4 ml of DMF is added all at once, at 0° C., to 5 ml of CH₂Cl₂ containing 61 mg of Bop and the TFA salt of 44 mg of the compound obtained in step 2. The mixture is neutralized by the addition of DIPEA and stirred for 24 hours. It is evaporated in vacuo at RT and an aqueous carbonate solution is then added. The precipitate is extracted with CH₂Cl₂. The extract is washed several times with an aqueous saline solution. It is dried (MgSO₄) and the solvent is then evaporated off. The solid obtained is chromatographed on silica gel, eluting with methanol/ chloroform mixtures containing increasing proportions of methanol.

M.p.=108°-110° C.

NMR SPECTRUM

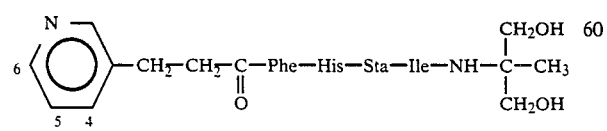

| Delta | Appearance | Protons | Assignment |
|---|---|---|---|
| 11.5-10.0 | broad s | 1 H | NH imidazole (H1) |
| 8.39-8.27 | m | 3 H | H2, H6 (C₅H₄N), NHCO |

-continued
NMR SPECTRUM

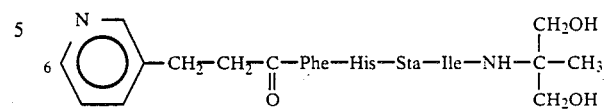

| Delta | Appearance | Protons | Assignment |
|---|---|---|---|
| 8.23 | d, J = 8 Hz | 1 H | NHCO |
| 7.75 | d, J = 8 Hz | 1 H | NHCO |
| 7.48 | s | 1 H | H2 (imidazole) |
| 7.42 | d, J approx. 8 Hz | 1 H | H4 (C₅H₄N) |
| 7.27 | s | 1 H | NH—C—CH₃ |
| 7.25-7.05 | m | 7 H | C₆H₅, H5 (C₅H₄N), NHCO |
| 6.79 | s | 1 H | H4 (imidazole) |
| 5.06-4.60 | m | 3 H | OH |
| 4.50-4.00 | m | 3 H | CH (alpha) |
| 3.81-3.64 | m | 2 H | CHNH and CHOH (Sta) |
| 3.50-3.00 | m | 4 H | CH₂OH and H₂O |
| 3.00-2.58 | m | 6 H | CH₂—C₆H₅, CH₂—imidazole, CH₂—C₅H₄N |
| 2.40-2.29 | m | 2 H | CH₂—CO |
| 2.19-1.95 | m | 2 H | CH₂—CO (Sta) |
| 1.08 | s | 3 H | CH₃—C—NH |
| 1.71-0.93 | m | 6 H | CH and CH₂ (Sta and Ile) |
| 0.84-0.65 | m | 12 H | CH₃ (Ile and Sta) |

EXAMPLE 5

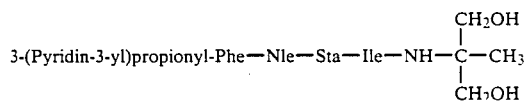

SR 43 707

This compound is prepared from SR 43 574 (138 mg) by following the procedure of Example 3.

Weight=60 mg.
m.p.=86°-87° C.

NMR SPECTRUM

| Delta | Appearance | Protons | Assignment |
|---|---|---|---|
| 8.34-7.06 | m | 14 H | C₅H₄N, C₆H₅, NHCO and NH—C—CH₃ |
| 4.80 | d, J approx. 4 Hz | 1 H | OH (Sta) |
| 4.69 | t, J approx. 4 Hz | 2 H | CH₂—OH |
| 4.58-4.00 | m | 3 H | CH (alpha) (Phe, Nle, Ile) |
| 3.84-3.67 | m | 2 H | CHOH and CHNH (Sta) |
| 3.50-3.25 | m | | CH₂OH and H₂O peak |

-continued

| NMR SPECTRUM | | | |
|---|---|---|---|
| Delta | Appearance | Protons | Assignment |
| 3.0–2.55 | m | 4 H | C$\underline{H_2}$C$_6$H$_5$, C$\underline{H_2}$C$_5$H$_4$N |
| 2.37–2.02 | m | 4 H | C$_5$H$_4$N—CH$_2$C$\underline{H_2}$CO, CH$_2$CO (Sta) |
| 1.10 | s | 3 H | NH—C(CH$_3$)—C$\underline{H_3}$ |
| 1.71–0.92 | m | 12 H | CH and CH$_2$ (Nle, Ile, Sta) |
| 0.92–0.68 | m | 15 H | CH$_3$ (Ile, Nle, Sta) |

EXAMPLE 6

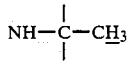

SR 43686

(1°) 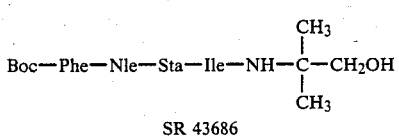

A solution of 0.534 g of 2-amino-2-methylpropanol in 5 ml of CH$_2$Cl$_2$ is added to a solution of 1 g of Boc-Ile-ONSu in 10 ml of CH$_2$Cl$_2$. After stirring for 20 minutes, the insoluble material is filtered off and the filtrate is then concentrated.

(2°) SR 43 686

The Boc group is removed, with 3 ml of TFA for 20 minutes at about 2° C., from 302 mg of the crude product obtained in the previous step. The residue is dissolved in 10 ml of CH$_2$Cl$_2$, the solution is adjusted to pH by 7 by the addition of NMM, and 535 mg of Boc-Phe-Nle-Sta-OH and 442 mg of Bop are then added. After stirring for 48 hours, the mixture is washed with an aqueous saline solution, a solution of KHSO$_4$, a solution of NaHCO$_3$ and water and then dried and concentrated. The residue is chromatographed on silica, eluting with ethyl acetate. The expected product crystallizes in the cold from ether.

| NMR SPECTRUM | | | |
|---|---|---|---|
| Delta | Appearance | Protons | Assignment |
| 6.91–7.90 | m including 4 d centered at 6.94–7.5–7.62–7.86, J = 8 Hz | 10 H | 5 H ar, 5 NH |
| 3.70–4.90 | m including one d centered at 4.85, J = 4 Hz | 7 H | OH (Sta), OH (CH$_2$OH), 3 H (alpha) (Phe, Nle, Ile), 2 H (Sta) |
| 2.02–3.38 | m | 8 H | C$\underline{H_2}$—OH, C$\underline{H_2}$—C$_6$H$_5$, C$\underline{H_2}$—NH, C$\underline{H_2}$—C(=O) (Sta) |
| 0.69–2.69 | m including 2 s at 1.23 and 1.11 | 36 H | (CH$_2$)$_3$ (Nle), CH$_2$—CH (Sta), Boc, 2 CH$_3$ of C(CH$_3$)(CH$_3$)—CH$_2$OH, CH$_3$ (Nle, Sta, Ile) |

EXAMPLE 7

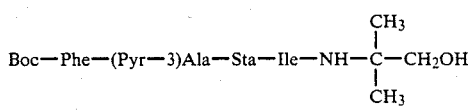

SR 43763

(1°) Ethyl (R,S)-2-acetamido-2-ethoxycarbonyl-3-(pyridin-3-yl) propionate 48 g of diethyl acetamidomalonate are added to a solution of 11 g of sodium in 300 ml of EtOH, the mixture is then heated to the reflux temperature, 36 g of 3-chloromethylpyridine hydrochloride are added and reflux is maintained for 5 hours. EtOH is evaporated off, the residue is taken up with water, the mixture is extracted and the extract is dried, concentrated and chromatographed on silica. A CH$_2$Cl$_2$/AcOEt mixture, 60/40 by volume, elutes 23 g of the expected compound.

(2°) (R,S)-(Pyr-3)Ala.2HCl 15 g of the previous diester are heated under reflux in 200 ml of 5 N HCl for 5 hours. The mixture is concentrated to dryness, EtOH is added and the mixture is evaporated. The process is repeated until the dihydrochloride recrystallizes: 15 g.

(3°) (R,S)-Boc-(Pyr-3)Ala 1 g of the previous dihydrochloride is dissolved in a mixture of equal volumes of water and dioxane. 350 mg of sodium hydroxide and 1 g of (Boc)$_2$O are added and the mixture is then stirred overnight at RT. The dioxane is evaporated off, water is added, the mixture is neutralized with 8 g of Amberlite CG 120 L (acid form) and stirred for 1 hour at RT and the medium is then transferred to a column containing 8 g of the same resin. Elution is carried out with distilled water until the pH reaches 5 and then with a 4% solution of ammonia in distilled water. The eluates are concentrated. 0.69 g of the expected product is collected.

(4°) Boc-(Pyr-3)Ala-Sta-OMe

A mixture of 465 mg of Sta-OMe.TFA and 500 mg of Boc-(Pyr-3)Ala is stirred for 3 days at RT in 10 ml of acetonitrile, in the presence of 780 mg of Bop, the medium being kept at about pH 7 by the addition of DIPEA. The mixture is then evaporated to dryness, water is added, extraction is carried out with AcOEt and the extract is washed with a solution of Na$_2$CO$_3$, water and an aqueous saline solution and then dried over MgSO$_4$ and evaporated to dryness. The residue is chromatographed on silica gel with a CH$_2$Cl$_2$/AcOEt eluting mixture, 1/9 by volume, which successively elutes:
  the less polar isomer A: 150 mg;
  the more polar isomer B: 180 mg.

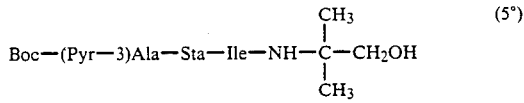

(5°)

The more polar isomer obtained in the previous step (600 mg) is hydrolized in a methanol/dioxane/water mixture (10/10/10 v/v/v) and 70 mg of sodium hydroxide are added. After 25 minutes, the starting material has disappeared. The mixture is concentrated to dryness, the residue is taken up with dioxane, and a solution of hydrogen chloride in ethyl acetate is added to pH 4. The medium is concentrated again, the concentrate is solubilized in 25 ml of acetonitrile, and DIPEA is added to pH 7. 500 mg of 2-isoleucylamino-2-methylpropane-1,3-diol trifluoroacetate, previously neutralized in acetonitrile with DIPEA, are then added, followed by 650 mg of Bop, the pH is adjusted to between 8 and 9 and the mixture is then stirred overnight at room temperature. The medium is concentrated and the concentrate is taken up with an aqueous carbonate solution and then ethyl acetate; the organic phase is washed with potassium bisulfate solution and then dried and concentrated. The crude product is chromatographed on silica; an ethyl acetate/methanol mixture (95/5 v/v) elutes the product, which is crystallized from a methanol/ether mixture. 420 mg are collected.

(6°) SR 43 763

This step is carried out in the usual way, starting from 390 mg of the previous compound and 250 mg of Boc-Phe-ONp. After chromatography on silica, eluting with an ethyl acetate/methanol mixture (90/10 v/v), 325 mg of the expected product are obtained.

| NMR SPECTRUM | | | |
|---|---|---|---|
| Delta | Appearance | Protons | Assignment |
| 8.48–7.05 | m | 13 H | H pyr, H ar, NHCO |
| 6.86 | d, J = 8 Hz | 1 H | $NHCO_2$ |
| 4.91–4.65 | m | 3 H | OH (Sta), $CH_2$—OH |
| 4.65–3.92 | m | 3 H | CH (alpha) (Phe, Ile, (Pyr-3)Ala) |
| 3.83–3.67 | m | 2 H | CHOH, CHNH (Sta) |
| 3.50–3.13 | m | — | $CH_2$—OH and $H_2O$ |
| 3.10–2.50 | m | 4 H | $CH_2C_6H_5$, $CH_2C_5H_4N$ |
| 2.16–1.90 | m | 2 H | $CH_2CO$ (Sta) |
| 1.70–1.00 | | } 18 H | $CH_2$ and CH (Sta), $CH_2$ and CH (Ile), $(CH_3)_3C$, $CH_3$ |
| 1.22 | s | | |
| 1.09 | s | | |
| 0.90–0.64 | m | 12 H | $CH_3$ (Sta), $CH_3$ (Ile) |

EXAMPLE 8

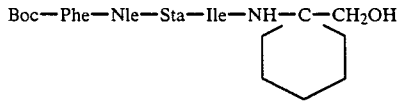

-continued
SR 43799

(1°) 1-N-Boc-isoleucylamino-1-methoxycarbonylcyclohexane

A mixture of Boc-Ile-OH (3.81 g), 1-amino-1-methoxycarbonylcyclohexane (2.6 g) and Bop (7.29 g) in methylene chloride is stirred for 48 hours. The organic phase is washed with water, potassium bisulfate and sodium carbonate, dried and concentrated. The concentrate is chromatographed on silica, eluting with an ethyl acetate/methylene chloride mixture (50/50 v/v), and the expected product is collected; it crystallizes on evaporation of the solvent.

Weight = 4.4 g.

m.p. = 152°–155° C.

$[\alpha]_D = = 39°$ (c = 1; MeOH).

(2°) 1-N-Boc-isoleucylamino-1-hydroxymethylcyclohexane 303 mg of sodium aluminum hydride are added in small portions to a solution of the previous product (1.5 g) in ether and the mixture is stirred for 4 hours at RT. The reaction medium is poured into an iced solution of potassium bisulfate and the ether phase is decanted, dried and concentrated in vacuo to give a white solid, which is chromatographed on silica. An ethyl acetate/hexane mixture (50/50 v/v) elutes the expected product, which crystallizes on evaporation of the solvents.

Weight = 1 g m.p. = 160°–162° C.

$[\alpha]_D = -28.2$ (C = 1; MeOH).

(3°) Sr 43799

This product is obtained by the usual coupling methods.

| NMR SPECTRUM | | | |
|---|---|---|---|
| Delta | Appearance | Protons | Assignment |
| 7.85 | d, J = 8 Hz | 1 H | NHCO |
| 7.62 | d, J = 8 Hz | 1 H | NHCO |
| 7.50 | d, J = 8 Hz | 1 H | NHCO |
| 7.27–7.08 | m | 5 H | $C_6H_5$ |
| 7.08 | s | 1 H | NHCO |
| 6.93 | d, J = 8 Hz | 1 H | NHCO |
| 4.85 | d, J = 4 Hz | 1 H | OH |
| 4.53 | t, J = 6 Hz | 1 H | $CH_2$—OH |
| 4.30–4.00 | m | 3 H | CH (alpha) (Phe, Nle, Ile) |
| 3.86–3.68 | m | 2 H | CHNH, CHOH (Sta) |
| 3.50–3.38 | m | 2 H | $CH_2OH$ |
| 2.96–2.55 | m | 2 H | $CH_2C_6H_5$ |
| 2.18–0.64 | m | 48 H | $(CH_3)_3$, $CH_2CO$ (Sta), CH, $CH_2$, $CH_3$ (Nle, Sta, Ile), $CH_2$ (cyclohexane) |

EXAMPLE 9

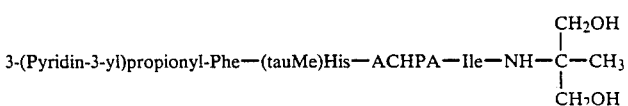

SR 43842

(1°) (tauMe)His-OMe.2HCl (tauMe)His is prepared by the method described in J.R. Neth. Chem. Soc., 1978, 97 293–295. 4.5 g of the dihydrochloride of this product are dissolved in 50 ml of MeOH; the solution is saturated with HCl gas at 10°–15° C. and then stirred at RT for 72 hours. It is concentrated to dryness and the residue is taken up twice in ether and then in acetone, from which it crystallizes; 4 g are obtained after filtration.

(2°) Boc-Phe-(tauMe)His-OMe 508 mg of the previous product are placed in 25 ml of CH₂Cl₂ and brought to pH 7 by the addition of DIPEA. 772 mg of Boc-Phe-ONp and 306 mg of HOBt are added. After stirring for 2 days at RT, the mixture is washed with iced water and then dried and concentrated. By chromatography on silica and elution with an AcOEt/MeOH mixture, 9/1 by volume, 849 mg of the expected product are collected.

(3°) Boc-Phe-(tauMe)His-ACHPA-OCH₃

800 mg of Boc-Phe-(tauMe)His-OMe are dissolved at 10° C. in 8 ml of a mixture of methanol and dioxane (166 vol/vol) and 90 mg of sodium hydroxide in 2 ml of water are then added. The temperature is kept at 10° C. for 1 hour and then at RT for 1 hour 30 minutes. The mixture is acidified to pH=3 with a solution of potassium bisulfate and then evaporated to dryness. The solid obtained is suspended in 20 ml of DMF at 0° C., in the presence of 820 mg of Bop, and the salt TFA.ACHPA-OCH₃ obtained from 620 mg of Boc-ACHPA-OCH₃, in 7 ml of DMF, is then added; finally, 500 mg of DIPEA are added. The pH is kept at 6–7 and the temperature is kept at between 0° C. and 10° C. for 2 hours, a further quantity of DIPEA is then added to bring the pH to 7 and the mixture is left to return to RT overnight. The solvent is evaporated off, an aqueous carbonate solution is added, extraction is carried out 3 times with ethyl acetate and the extracts are washed several times with an aqueous carbonate solution, water and an aqueous saline solution, dried and evaporated in vacuo. The solid is crystallized from a methanol/isopropyl ether mixture and then recrystallized in the cold from the minimum quantity of methanol to give 415 mg.

M.p.=164°–166° C.

$[\alpha]_D = -34.3$ (c=0.61; MeOH). (4°) 3-(Pyridin-3-yl)propionyl-Phe-(tauMe)His-ACHPA-OCH₃

The trifluoroacetic acid salt of 364 mg of the product obtained in the previous step is prepared. This salt is placed in 10 ml of acetonitrile, 114 mg of 3-(pyridin-3-yl)propionic acid and 336 mg of Bop are added and the mixture is neutralized by the addition of DIPEA; the medium becomes homogeneous and a precipitate then appears. The solid is filtered off the next day and washed with water and ether (solid 1). Aqueous sodium carbonate is added to the filtrate, the acetonitrile is evaporated off and extraction is carried out with ethyl acetate. The insoluble material which appears in the organic phase is filtered off; the filtrate is dissolved in a solution of potassium bisulfate and then reprecipitated by the addition of sodium bicarbonate (solid 2). The solids 1 and 2 are identical and correspond to the expected product.

Weight=215 mg.

m.p.=211°–215° C.

$[\alpha]_D = -36.7$ (c=0.27; MeOH).

(5°) SR 43842

The compound obtained above (206 mg) is acidified in the following manner. It is suspended in a mixture of water (4 ml) and methanol (10 ml), after which 5 drops of 30% sodium hydroxide solution, 4 ml of DMF and a further 5 drops of 30% sodium hydroxide solution are added. After stirring for 2 hours, it is seen that an almost complete solution has been formed. The insoluble material is filtered off, the methanol is evaporated off and the mixture is acidified to about pH 4–5 with a solution of potassium bisulfate and evaporated to dryness. The residue is treated at 0° C. with 2 ml of TFA and 86 of

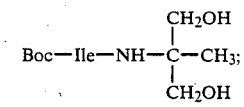

after evaporation, the residue is dissolved in 3 ml of DMF and neutralized with DIPEA. The TFA salt formed, the previous acid and 124 mg of Bop are mixed in 5 ml of DMF; the mixture is cooled to 0° C., DIPEA is added in a sufficient quantity to bring the pH to about 7–8 and the mixture is left to return to RT. After 3 days, the DMF is evaporated off, an aqueous carbonate solution is added and extraction is carried out with 3 volumes of an aqueous carbonate solution, water and an aqueous saline solution. After evaporation, a white solid is obtained (75 mg) which recrystallizes from an MeOH/ AcOEt mixture (27 mg).

M.p.=119°–124° C.

The mother liquor from crystallization is chromatographed on silica.

| | NMR SPECTRUM | | |
|---|---|---|---|
| Delta | Appearance | Protons | Assignment |
| 8.40–8.24 | m | 3 H | 2 H ortho pyr, 1 NHCO |
| 8.17 | d, J = 8 Hz | 1 H | NHCO |
| 7.71 | d, J = 8 Hz | 1 H | NHCO |
| 7.45–7.07 | m | 10 H | 1 H (tauMe), 2 H pyr, 5 H ar, NHCO and NHC—CH₃ |
| 6.82 | s | 1 H | 1 H (tauMe)His |
| 4.92 | broad s | 1 H | OH (ACHPA) |
| 4.71 | t, (J approx. 4 Hz) | 2 H | CH₂—OH |
| 4.50–3.62 | m | 5 H | CH (alpha) (Phe, (tauMe)His, Ile), CHNH, CHOH (ACHPA) |
| 3.50 | s | 3 H | CH₃ (tauMe)His |
| 3.50–3.07 | m | 4 H | CH₂OH (H₂O) |
| 3.07–2.58 | m | 6 H | CH₂—C₅H₄N, CH₂—C₆H₅, CH₂—imidazole |
| 2.43–2.27 | m | 2 H | CH₂—CO—Phe |
| 2.12–2.00 | m | 2 H | CH₂CO (ACHPA) |
| 1.75–0.91 | m | 16 H | CH, CH₂ (ACHPA, Ile) |
| 1.08 | s | | CH₃ (diol) |
| 0.91–0.56 | m | 6 H | CH₃ (Ile) |

The following compounds (Table 2) were prepared by using the same methods. They are characterized by their NMR spectra.

TABLE 2

SR 43 721

TABLE 2-continued

Boc—Phe—Nle—ACHPA—Ile—NH—C(CH₂OH)(CH₃)(CH₂OH)

$$\text{Boc—Phe—Nle—ACHPA—Ile—NH—C(CH}_2\text{OH)(CH}_3\text{)(CH}_2\text{OH)}$$

SR 43 808

3-(Pyridin-3-yl)propionyl-Phe—Nle—ACHPA—Ala—NH—C(CH₂OH)(CH₃)(CH₂OH)

SR 43 845

3-(Pyridin-3-yl)propionyl-Phe—His—ACHPA—Ile—NH—C(CH₂OH)(CH₃)(CH₂OH)

SR 43 860

Boc—Phe—Nle—Sta—Ala—NH—C(CH₃)(CH₂OH)(CH₃)

SR 43 925

Nicotinoyl-Phe—His—ACHPA—Ile—NH—C(CH₂OH)(CH₃)(CH₂OH)

SR 43 966

3-(Pyridin-3-yl)propionyl-Phe—(tauMe)His—Sta—Ile—NH—C(CH₃)(CH₂OH)(CH₃)

SR 43 972

3-(Pyridin-3-yl)propionyl-Phe—His—Sta—Ile—NH—C(CH₂OH)(CH₃)(CH₂OH)

SR 44 094

Boc—Phe—Nle—Sta—Ile—NH—C(CH₂OH)(CH₂OH)(CH₂OH)

SR 44 125

Boc—Phe—(benzimidazol-2-yl)Ala—ACHPA—Ile—NH—C(CH₂OH)(CH₃)(CH₂OH)

SR 44 177

3-(Pyridin-3-yl)propionyl-Phe—His—ACHPA—Ile—NH—C(CH₃)(CH₂OH)(CH₃)

SR 43 721

| Delta | Appearance | Protons | Assignment |
|---|---|---|---|
| 7.91 | d, J = 8 Hz | 1 H | NHCO |
| 7.67 | d, J = 8 Hz | 1 H | NHCO |
| 7.48 | d, J = 8 Hz | 1 H | NHCO |
| 7.27–7.07 | m | 6 H | C₆H₅, NH—C(CH₃) |
| 6.95 | d, J = 8 Hz | 1 H | NHCO₂ |
| 4.85 | d, J approx. 4 Hz | 1 H | OH (ACHPA) |
| 4.68 | t, J approx. 4 Hz | 2 H | CH₂—OH |
| 4.31–4.0 | m | 3 H | CH (alpha) (Phe, |

TABLE 2-continued

| | | | |
|---|---|---|---|
| 3.90–3.68 | m | 2 H | Nle, Ile)<br>CHOH and<br>CHNH (ACHPA) |
| 3.50–3.19 | m | | CH$_2$OH and H$_2$O<br>peak |
| 2.98–2.57 | m | 2 H | CH$_2$C$_6$H$_5$ |
| 2.23–2.00 | m | 2 H | CH$_2$—CO (ACHPA) |
| 1.23 | s | | C(CH$_3$)$_3$ |
| 1.08 | s | | CH$_3$—C—NH |
| 1.77 | m | 31 H | CH and CH$_2$ (Nle and Ile),<br>CH and CH$_2$ (ACHPA), |
| 0.66 | m | | CH$_3$ (Nle and Ile) |

SR 43 808

| | | | |
|---|---|---|---|
| 7.1–8.32 | complex m<br>including 4 d<br>centered at<br>7.33, 7.42, 8.07,<br>J = 6 Hz | 14 H | 5 NHCO, 5 H ar,<br>4 H pyr |
| 3.24–4.83 | complex m<br>including 1 d<br>centered at 4.83,<br>J = 6 Hz | 12 H | OH (ACHPA),<br>2 OH (diol),<br>H (alpha) (Phe,<br>Nle, Ala), CH—OH<br>and CH—NH<br>(ACHPA), 2 CH$_2$—OH |
| 2.04–3 | complex m<br>including 2 t<br>centered at 2.13<br>and 2.63 | 8 H | CH$_2$—C$_6$H$_5$, CH$_2$—<br>pyr, 2 CH$_2$—CO |
| 0.49–1.75 | complex m<br>including 1 s<br>at 1.07 and 1 s<br>at 0.81 | 27 H | 9 CH$_2$ (Nle,<br>ACHPA), 1 CH$_3$<br>(Ala), 1 CH$_3$<br>(diol), 1 CH$_3$<br>(Nle) |

SR 43 845

| | | | |
|---|---|---|---|
| 8.40–8.78 | m | 3 H | 2 H ortho pyr,<br>1 NHCO |
| 8.22 | d, J = 8 Hz | 1 H | NHCO |
| 7.66 | d, J = 8 Hz | 1 H | NHCO |
| 7.48 | s | 1 H | CH im |
| 7.42 | d, J = 8 Hz | 1 H | NHCO |
| 7.26 | s | 1 H | NH—C— |
| 7.23–7.07 | m | 7 H | 5 H ar, 2 H pyr |
| 6.78 | broad s | 1 H | CH im |
| 4.92 | broad s | 1 H | OH (ACHPA) |
| 4.71 | t, J approx. 4 Hz | 2 H | CH$_2$—OH |
| 4.50–3.62 | m | 5 H | CH (alpha) (Phe,<br>His, Ile), CHOH<br>and CHNH (ACHPA) |
| 3.50–3.07 | m | 4 H | CH$_2$OH (H$_2$O) |
| 3.07–2.58 | m | 6 H | CH$_2$—C$_5$H$_4$N,<br>CH$_2$—C$_6$H$_5$,<br>CH$_2$—imidazole |
| 2.43–2.27 | m | 2 H | CH$_2$—CO—Phe |
| 2.12–2.00 | m | 2 H | CH$_2$—CO (ACHPA) |
| 1.75–0.91 | m | 16 H | CH and CH$_2$ (Ile,<br>ACHPA) |
| 1.08 | s | 3 H | CH$_3$ (diol) |
| 0.91–0.56 | m | 6 H | CH$_3$ (Ile) |

SR 43 860

| | | | |
|---|---|---|---|
| 7.90–6.86 | m | 10 H | 5 H ar, NHCO$_2$,<br>3 NHCO, NH—C— |
| 4.82 | d, J = 4 Hz | 1 H | OH |
| 4.66 | m | 2 H | OH |

TABLE 2-continued

| | | | |
|---|---|---|---|
| 4.29–3.68 | m | 5 H | CH (alpha) (Phe, Nle, Ala), CHNH and CHOH (Sta) |
| 3.50–3.25 | m | | CH₂OH and H₂O |
| 2.97–2.56 | m | 2 H | CH₂ (Phe) |
| 2.14–2.0 | m | 2 H | CH₂CO (Sta) |
| 1.68–1.0 | m | 24 H | CH₂ (Nle), CH and CH₂ (Sta), CH₃ at 1.08, (CH₃)₃C— at 1.25 |
| 0.89–0.71 | m | 9 H | CH₃ (Nle and Sta) |

SR 43 966

| | | | |
|---|---|---|---|
| 8.42–8.18 | m | 4 H | 2 H ortho pyr, NHCO (His and Phe) |
| 7.65 | d, J = 8 Hz | 1 H | NHCO (Ile) |
| 7.46–7.04 | m | 10 H | 2 H pyr, H im, 5 H ar, NHCO (Sta), $$NH-\underset{|}{\overset{|}{C}}-$$ |
| 6.81 | s | 1 H | H im |
| 4.97–4.70 | m | 2 H | OH (Sta), CH₂—OH |
| 4.50–4.30 | m | 2 H | CH (alpha) (Phe, His) |
| 4.05 | t, J approx. 8 Hz | 1 H | CH (alpha) (Ile) |
| 3.77–3.61 | m | 2 H | CHNH and CHOH (Sta) |
| 3.43–3.19 | m | | CH₂OH and H₂O |
| 3.50 | s | 3 H | N—CH₃ |
| 3.02–2.57 | m | 6 H | CH₂ (Phe, His, C₅H₄N) |
| 2.41–2.27 | m | 2 H | CH₂CO |
| 2.14–1.97 | m | 2 H | CH₂CO (Sta) |
| 1.70–0.90 | m | 12 H | CH and CH₂ (Ile), CH and CH₃ (Sta), $$CH_3, NH-\underset{\underset{CH_2-OH}{|}}{\overset{|}{C(CH_3)_2}}$$ |
| 0.90–0.61 | m | 12 H | CH₃ (Ile) CH₃ (Ala) |

SR 43 972

| | | | |
|---|---|---|---|
| 11.80 | broad s | 1 H | 5 NH im |
| 8.44–8.17 | m | 4 H | 2 H ortho pyr, 2 H NHCO |
| 7.70 | d, J = 8 Hz | 1 H | NHCO |
| 7.50–7.03 | m | 10 H | 2 NHCO + H im, 5 H ar, 2 H pyr |
| 6.79 | s | 1 H | H im |
| 4.95–3.62 | m | 8 H | 3 OH, CH (alpha) (Phe, His, Ile), CHNH and CHOH (Sta) |
| 3.50–3.14 | m | | CH₂OH (and H₂O) |
| 3.06–1.91 | m | 10 H | CH₂ (His, Phe), CH₂ (C₅H₄N), CH₂CO (Sta), CH₂—CH₂—CO |
| 1.71–0.91 | m | 8 H | CH and CH₂ (Sta and Ile), CH₂—CH₂—CH₂—CO |
| 1.08 | s | 3 H | CH₃ |
| 0.91–0.55 | m | 12 H | CH₃ (Ile and Sta) |

SR 44 094

| | | | |
|---|---|---|---|
| 7.90–6.87 | m | 10 H | 5 H ar, 1 NHCO₂, 3 NHCO, $$NH-\underset{|}{\overset{|}{C}}-$$ |
| 4.83 | d, J = 4 Hz | 1 H | OH |
| 4.62 | m | 3 H | OH |
| 4.31–3.41 | m | 11 H | CH (alpha) (Phe, Nle, Ile), CH |

TABLE 2-continued

| | | | |
|---|---|---|---|
| 2.98–2.57 | m | 2 H | and CHOH (Sta), CH$_2$OH C$\underline{H_2}$C$_6$H$_5$ |
| 2.29–2.00 | m | 2 H | CH$_2$CO (Sta) |
| 1.70–0.63 | m | other | aliphatic CH, CH$_2$ and CH$_3$ |
| | | SR 44 125 | |
| 12.2 | broad s | 1 H | NH (benzimidazole) |
| 8.48–6.96 | m | 14 H | 5 H ar, C$_6$H$_4$ (benzimidazole), NHCO$_2$, NHCO, NH—C— |
| 5.26 | d, J = 5 Hz | 1 H | OH (ACHPA) |
| 4.78–4.61 | m | 3 H | CH$_2$—OH, CH (alpha) (benzimidazole) |
| 4.23–3.67 | m | 4 H | CH (alpha) (Phe, Ile), C$\underline{H}$NH and C$\underline{H}$OH (ACHPA) |
| 3.50–2.59 | m | | CH$_2$OH, CH$_2$ (Phe), CH$_2$ (benzimidazole) |
| 2.27–2.08 | m | 2 H | CH$_2$CO (ACHPA) |
| 1.75–0.55 | m | 34 H | CH and CH$_2$ (ACHPA), CH, CH$_2$, CH$_3$ (Ile), —C(CH$_3$)$_3$, —CH$_3$ |
| | | SR 44 177 | |
| 11.81 | broad s | 1 H | NH (imidazole) |
| 8.42–7.05 | m | 13 H | NHCO, NH—C—, 4 H pyr, H im, 5 H ar |
| 6.80 | broad s | 1 H | CH im |
| 5.0–5.49 | broad m | 2 H | OH |
| 4.5–4.34 | m | 2 H | CH (alpha) (Phe and His) |
| 4.05 | t, J = 8 Hz | 1 H | CH (alpha) (Ile) |
| 3.82–3.65 | m | 2 H | C$\underline{H}$NH and C$\underline{H}$OH (ACHPA) |
| 3.40–3.20 | m | 2 H | C$\underline{H_2}$OH (H$_2$O) |
| 3.05–2.27 | m | 8 H | C$\underline{H_2}$—C$_6$H$_5$, C$\underline{H_2}$—imidazole, C$\underline{H_2}$—pyridine, C$\underline{H_2}$CO (Phe) |
| 2.17–1.97 | m | 2 H | CH$_2$CO (ACHPA) |
| 1.74–0.94 | m | 22 H | CH and CH$_2$ (ACHPA, Ile), CH$_3$ |
| 0.91–0.55 | m | 6 H | CH$_3$ (Ile) |

[α]$_D$ = −35.5° (c = 0.21; methanol);
m.p. = 132–137° C. (after solidification in hexene).
M.P. = 125–128° C. (triturated in ether);
[α]$_D$ = −32.3° (c = 0.6; methanol).

What is claimed is:

1. A peptide amino-alcohol derivative of the formula:

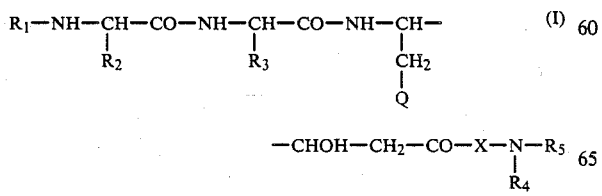

in which:

R$_1$ represents an acyl group chosen from the following groups: alkylcarbonyl, alkoxycarbonyl, arylcarbonyl, arylalkylcarbonyl, arylalkoxycarbonyl, heterocyclylcarbonyl, heterocyclylalkylcarbonyl, in which the alkyl group is optionally substituted by a hydroxyl group, heterocyclylcarbonylalkylcarbonyl, heterocyclylalkenylcarbonyl and cycloalkylcarbonyl, or represents a (lower alkyl)sulfonyl group which is unsubstituted or substituted on the alkyl by a free amino group or an amino group carrying a protecting group, or by a phenyl, or represents a phenylsulfonyl group which is unsubstituted or substituted on the phenyl nucleus by a lower alkyl;

$R_2$ represents a lower alkyl group which is unsubstituted or substituted by a phenyl, naphthyl, cyclohexyl or pyridyl, or $R_2$ represents a phenyl, naphthyl, cyclohexyl or pyridyl radical;

$R_3$ represents hydrogen, a lower alkenyl, a phenyl, a naphthyl, a cycloalkyl containing 3 to 6 carbon atoms, a 5-membered or 6-membered monocyclic heterocyclic group which is unsubstituted or substituted with a lower alkyl or trifluoromethyl, or alternatively a lower alkyl which is unsubstituted or substituted by a free amino group or an amino group carrying a protecting group, by a di(lower alkyl)amino group, by a free carboxyl or a carboxyl esterified with a lower alkyl or a benzyl, by a free carbamoyl or a carbamoyl substituted with one or two lower alkyls or with a phenyl, by a hydroxyl, lower alkoxy or benzyloxy group, by a pyridylmethoxy group, by a (lower alkyl)thio, (lower alkyl)sulfinyl or (lower alkyl)sulfonyl group, by a phenyl which is unsubstituted or substituted with a hydroxyl, by a naphthyl, by a cycloalkyl containing from 3 to 6 carbon atoms, by a 5-membered or 6-membered monocyclic heterocyclic group which is unsubstituted or substituted with a lower alkyl or a trifluoromethyl, or by a bicyclic heterocyclic group which is unsubstituted or substituted with a lower alkyl or a trifluoromethyl;

$R_4$ represents hydrogen or a lower alkyl which is unsubstituted or substituted by an indolyl, pyridyl, imidazolyl or phenyl radical;

$R_5$ represents an aliphatic or cyclic hydrocarbon group of 3 to 20 carbon atoms which is unsubstituted or substituted by a phenyl, hydroxyphenyl or amino group, the said hydrocarbon group containing at least one hydroxyl group and at least one carbon atom not having a C—H bond;

Q represents isopropyl, phenyl or cyclohexyl, respectively forming with the radical:

$$-NH-CH-CHOH-CH_2-CO-$$
$$\phantom{-NH-}|$$
$$\phantom{-NH-}CH_2$$
$$\phantom{-NH-}|$$

the residue of the amino acid Sta, AHPPA or ACHPA; and

X is either a direct bond or the residue of an amino acid such as Ala, Nva, Val, Leu, Nle, Ile, Phg, Abu or Cpg;

and also any pharmaceutically acceptable salts of the said peptide amino alcohol with mineral or organic acids or with alkali metals or alkaline earth metals.

2. A peptide amino-alcohol derivative as claimed in claim 1 of the formula:

$$R_1-NH-CH(R_2)-CO-NH-CH(R_3)-CO-NH-CH(CH_2Q)-CHOH-CH_2-CO-X-N(R_4)-(CH_2)_p-C(CH_2OH)(CHR_6OH)-(CH_2)_qR_7$$

in which $R_1$, $R_2$, $R_3$, Q, X and $R_4$ are as defined in claim 1, p represents an integer between zero and five,
q represents an integer between 0 and five,
$R_6$ represents hydrogen or a lower alkyl, and
$R_7$ represents hydrogen, or a hydroxyl group, an amino group, a carboxyl group, a pyridyl group or a phenyl group which is unsubstituted or substituted by a hydroxyl, with the proviso that if Q=0, $R_7$ is different from hydrogen.

3. A peptide amino-alcohol derivative as claimed in claim 1, of the formula:

$$R_1-NH-CH(R_2)-CO-NH-CH(R_3)-CO-NH-CH(CH_2Q)-CHOH-CH_2-CO-X-N(R_4)-(CH_2)_p-C(R_8)(R_9)-CH_2OH$$

in which $R_1$, $R_2$, $R_3$, Q, X and $R_4$ are as defined in claim 1, p represents an integer between zero and 5,
$R_8$ represents a lower alkyl, and
$R_9$ represents a lower alkyl which is unsubstituted or substituted by a free amino group or an amino group carrying a protecting group, or
$R_8$ and $R_9$ together form a cycloalkyl of 3 to 8 carbon atoms with the carbon atom to which they are joined.

4. A peptide amino-alcohol derivative as claimed in claim 1, wherein $R_1$ represents one of the following groups:

$$(CH_3)_3C-O-\underset{\underset{O}{\|}}{C}-$$

$$(CH_3)_2CH-CH_2-\underset{\underset{O}{\|}}{C}-$$

$$C_6H_5-(CH_2)_a-\underset{\underset{O}{\|}}{C}-, \text{ in which } a = 0, 1 \text{ or } 2$$

$$(C_6H_5-CH_2)_2CH-\underset{\underset{O}{\|}}{C}-$$

$$C_6H_5-CH_2-O-\underset{\underset{O}{\|}}{C}-$$

$$\underset{\underset{4}{}}{\overset{\overset{2}{N}}{\underset{3}{\bigcirc}}}-(CH_2)_b-\underset{\underset{O}{\|}}{C}-, \text{ in which } b = 0, 1, 2, 3, 4, 5 \text{ or } 6$$

-continued

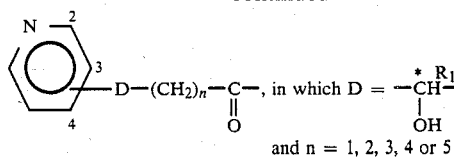

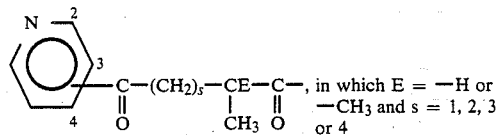

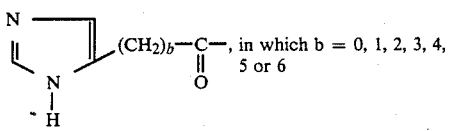

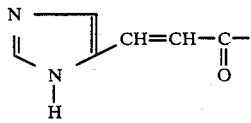

NH₂CH₂CH₂—SO₂—
BocNHCH₂CH₂—SO₂—
ZNHCH₂CH₂—SO₂—
A—SO₂—, in which A is a lower alkyl
C₆H₅—(CH₂)ₐ—SO₂—, in which a=0, 1 or 2
or one of any salts of the said peptide amino alcohols with pharmaceutically acceptable mineral or organic acids.

5. A peptide amino-alcohol derivative as claimed in claim 1, wherein $R_1$ represents a group chosen from the following groups:
isovaleryl,
4-(pyridin-2-yl)-4-oxobutyryl,
4-(pyridin-2-yl)-4-hydroxybutyryl,
3-(pyridin-3-yl)propionyl,
4-(pyridin-3-yl)butyryl,
nicotinoyl and
benzenesulfonyl.

6. A peptide amino-alcohol derivative as claimed in claim 1, wherein $R_5$ contains from 1 to 3 hydroxyl groups.

7. A peptide amino-alcohol derivative as claimed in claim 1, wherein $R_3$ is such that the residue —NH—CH($R_3$)—CO— represents the residue (tauMe)His.

8. A peptide amino-alcohol derivative of the formula:

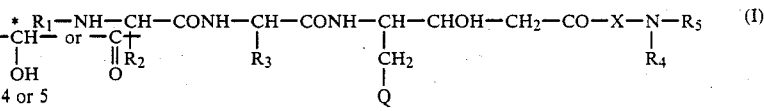

in which:
$R_1$ represents a group chosen from the following groups: isovaleryl, tert.-butoxycarbonyl, 3-(pyridin-3-yl)propionyl, 4-(pyridin-3-yl)butyryl and nicotinoyl;
$R_2$ represents a benzyl;
$R_3$ represents n-butyl or a methyl substituted by a heterocyclic radical chosen from imidazol-4-yl, 1-methylimidazol-4-yl, 2-methylimidazol-4-yl, pyridin-3yl and benzimidazol-2-yl;
$R_4$ is hydrogen;
Q represents isopropyl, phenyl or cyclohexyl, respectively forming with the radical:

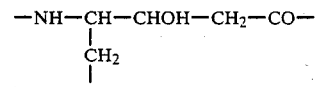

the residue of the amino acid Sta, AHPPA or ACHPA;
X represents the residue of one of the amino acids Ile or Ala; and
$R_5$ represents an aliphatic or cyclic hydrocarbon group of 3 to 20 carbon atoms which is unsubstituted or substituted by a phenyl or hydroxyphenyl group, the said hydrocarbon group simultaneously containing at least one hydroxyl group and at least one carbon atom not having a C—H bond;
and also any pharmaceutically acceptable salts of the said peptide amino alcohol with mineral or organic acids or with alkali metals or alkaline earth metals.

9. A peptide amino-alcohol derivative as claimed in claim 8, in which $R_5$ represents a group chosen from:

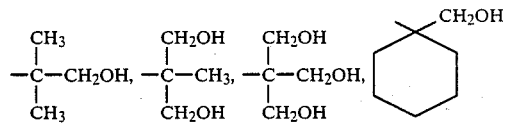

10. A pharmaceutical composition for inhibition of renin-angiotensin enzyme systems which contains an renin-angiotensin enzyme inhibiting amount, as the active ingredient, of the product as claimed in claim 1.

11. A pharmaceutical composition which contains, as the active ingredient, from 1 to 1000 mg of a product as claimed in claim 1, per dosage unit, mixed with a pharmaceutical excipient.

12. A pharmaceutical composition which contains, as the active ingredient, a product as claimed in claim 8.

13. A pharmaceutical composition which contains, as the active ingredient, from 1 to 1000 mg of a product as claimed in claim 8, per dosage unit, mixed with a pharmaceutical excipient.

* * * * *